United States Patent [19]
Nakano et al.

[11] Patent Number: 5,101,038
[45] Date of Patent: Mar. 31, 1992

[54] NOVEL SUBSTANCE DC 113 AND PRODUCTION THEREOF

[75] Inventors: Hirofumi Nakano; Isami Takahashi, both of Tokyo; Isao Kawamoto, Kanagawa; Toru Yasuzawa, Osaka; Keiichi Takahashi; Eiji Kobayashi, both of Shizuoka, all of Japan

[73] Assignee: Kyowa Hakko Kogyo Co., Ltd., Tokyo, Japan

[21] Appl. No.: 458,543

[22] Filed: Dec. 28, 1989

[30] Foreign Application Priority Data

Dec. 28, 1988 [JP] Japan ................ 63-332304

[51] Int. Cl.$^5$ .............. C07D 487/04; A61K 31/40
[52] U.S. Cl. .................. 548/421; 435/119; 514/410
[58] Field of Search ............ 548/421; 514/410

[56] References Cited

U.S. PATENT DOCUMENTS

| | | | |
|---|---|---|---|
| 4,169,888 | 10/1979 | Hanka et al. | 424/121 |
| 4,400,518 | 8/1983 | Wierenga | 548/433 |
| 4,413,132 | 11/1983 | Wierenga | 548/491 |
| 4,423,228 | 12/1983 | Wierenga | 548/421 |
| 4,423,229 | 11/1983 | Wierenga | 548/421 |
| 4,423,230 | 12/1983 | Wierenga | 548/433 |

FOREIGN PATENT DOCUMENTS

| | | |
|---|---|---|
| 0154445 | 9/1985 | European Pat. Off. . |
| 271581 | 6/1988 | European Pat. Off. . |
| 0318056 | 5/1989 | European Pat. Off. . |
| 2115184 | 4/1990 | Japan ................ 548/421 |
| 2087884 | 6/1982 | United Kingdom . |

OTHER PUBLICATIONS

*Adv. Enzyme Regulation,* Wierenga, et al. "Antitumor Activity and Biochemistry of Novel Analogs of the Antibiotic, CC-1065", vol. 22, p. 141 (1986).

*J. Medicinal Chemistry,* Warpehoski, M. A. et al., "Stereoelectronic Factors Influencing the Biological Activity and DNA Interaction of Synthetic Antitumor Agents Modeled on CC-1065," vol. 31, No. 3, p. 590 (1988).

*Primary Examiner*—Mary C. Ceperley
*Attorney, Agent, or Firm*—Fitzpatrick, Cella, Harper & Scinto

[57] ABSTRACT

A novel fermentation product, DC113, represented by the formula

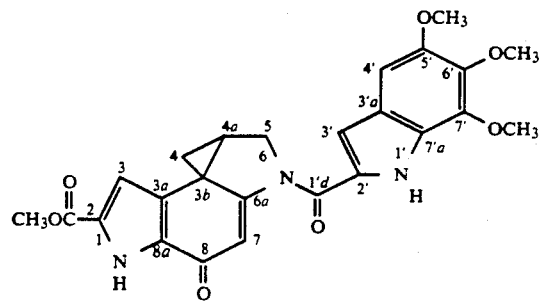

which has antimicrobial and antitumor activities.

1 Claim, No Drawings

NOVEL SUBSTANCE DC 113 AND PRODUCTION THEREOF

FIELD OF THE INVENTION

This invention relates to a novel antitumor antibiotic, DC 113, which has a dienone structure conjugated with a cyclopropane ring, to a method of producing it, pharmaceutical compositions containing it and to therapeutic methods using same.

BACKGROUND OF THE INVENTION

A known antitumor antibiotic, CC-1065, has a dienone structure conjugated with a cyclopropane ring (CRC Handbook of Antibiotic Compounds, 11, 502, CRC Press, U.S.A., 1985).

Analogs or related compounds, DC-88A and DC-89A1, are disclosed in WO87/06265 and DC-89A2, DC-89B1 and DC-89B2 in U.S. Patent application Ser. No. 380,379 filed on July 17, 1989.

SUMMARY OF THE INVENTION

An object of the present invention is to provide a novel antibiotic having an inhibitory effect on certain tumors.

The present inventors collected a large number of microorganisms from the natural world and tested them for their ability to produce antibiotics and, as a result, found that a microorganism (hereinafter referred to as "strain DO-113") isolated from a soil sample collected in Nakagyo-ku, Kyoto, Japan, when grown in a medium, can produce an antibiotic having an inhibitory effect on certain tumors in the culture medium.

The antibiotic was isolated and purified and examined for physicochemical characteristics. As a result, it was found to be a novel substance which shows strong antimicrobial and an inhibitory effect on certain tumors and was named "DC 113". DC 113 is more stable than the known compound DC-88A which has a related cyclopropane ring structure.

Thus, the invention provides the novel substance DC 113 having the formula

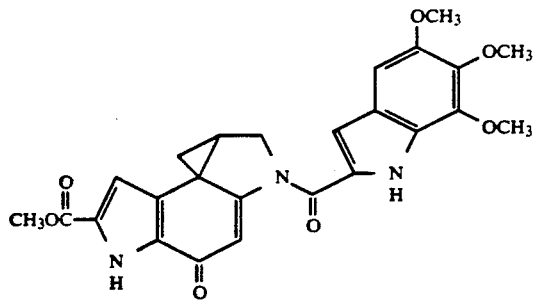

This novel substance has an inhibitory effect on certain tumors and antimicrobial activity. Methods of producing this novel substance using a microorganism belonging to the genus Streptomyces and capable of producing the novel substance are also described as well as methods of using this novel substance for therapeutic benefit and pharmaceutical compositions used in such treatments.

DETAILED DESCRIPTION OF THE INVENTION

DC 113 has the following physicochemical characteristics:

(1) Molecular weight: 477.
(2) Molecular formula $C_{25}H_{23}N_3O_7$.
(3) Mass spectrometric analysis: SIMS 478 $(M+1)^+$, EIMS 477 $(M)^+$.
(4) Specific rotation $[\alpha]$: $+180°$ (c=0.1, methanol).
(5) Ultraviolet absorption spectrum (measured in methanol): λmax: 235 nm (sh, $\epsilon=21,000$), 316 nm (sh, $\epsilon=16,000$), 367 nm {sh, $\epsilon=27,000$).
(6) Infrared absorption spectrum (measured in $CHCl_3$): 3460, 1714, 1642, 1619, 1517, 1489, 1399, 1382, 1300, 1258, 1215 (sh), 1106 $cm^{-1}$.
(7) PMR spectrum (measured in $CDCl_3$, with TMS as internal standard): δ(ppm): 9.98 (1H, brS), 9.29 (1H, brS), 7.02 (1H, s), 6.94 (1H, d, J=2.3Hz), 6.78 (1H, s), 6.60 (1H, d, J=2.3Hz), 4.46, 4.39 (2H, AB in ABX, $J_{AB}=10.4$, $J_{AX}=4.8$, $J_{BX}<1Hz$), 4.07 (3H, s), 3.94 (3H, s), 3.91 (3H, s), 3.89 (3H, s), 2.78 (1H, m), 1.75 (1H, dd, J=7.6, 4.5 Hz), 1.57 (1H, dd, J=4.7, 4.5 Hz).
(8) CMR spectrum (measured in $CDCl_3$, with TMS as internal standard): δ(ppm): 177.9 (s), 161.6 (s), 161.2 (s), 161.0 (s), 150.6 (s), 141.2 (s), 138.9 (s), 131.6 (s), 129.9 (s), 128.5 (s), 126.8 (s), 126.4 (s), 123.3 (s), 112.6 (d), 107.8 (d), 107.6 (d), 97.8 (d), 61.5 (q), 61.2 (q), 56.3 (q), 54.9 (t), 52.1 (q), 31.4 (s), 26.0 (t), 23.6 (d).
(9) Solubility: Soluble in chloroform, DMSO, methanol, ethyl acetate and acetone; sparingly soluble in water and n-hexane.
(10) Color reaction: Positive to Ehrlich reagent.
(11) Color and nature: Light-yellow basic substance.
(12) Thin layer chromatography [silica gel thin layer (HPTLC plate Art. 15647, E. Merck)]; developing solvent: toluene-acetone (7:3, v/v)] Rf=0.38 (After development, the spot of DC 113 can be detected by bioassay using Bacillus subtilis, using hot sulfuric acid or Ehrlich reagent, or by ultraviolet absorption.)

DC 113 has the following biological activities:

Antimicrobial activity

Minimum inhibitory concentrations (MIC) against various bacteria were determined by the agar dilution method (pH 7.0). The results are shown below in Table 1.

TABLE 1

| Test organism | MIC (μg of DC 113/ml) |
| --- | --- |
| Staphylococcus aureus ATCC 6538P | 0.0013 |
| Bacillus subtilis No. 10707 | 0.00065 |
| Klebsiella pneumoniae ATCC 10031 | 0.021 |
| Salmonella typhosa ATCC 9992 | 0.10 |
| Escherichia coli ATCC 26 | 0.064 |

Acute toxicity ($LD_{50}$)

Intravenous $LD_{50}$ in mice: 0.14 mg/kg

Therapeutic effect upon lymphocytic leukemia P-388 tumor

Lymphocytic leukemia P-388 tumor cells ($1 \times 10^6$ cells) were transplanted intraperitoneally into each of five $CDF_1$ male mice weighing about 22 grams. Twenty-four hours after transplantation, 0.2 ml of a PBS (phosphate-buffered saline) solution of DC 113 was intraperitoneally administered to each mouse. For comparison, 0.2 ml of a PBS solution of mitomycin C was intraperitoneally administered to each of five mice 24 hours after transplantation. The life-prolonging effect of DC 113 thus established is shown below in Table 2 in terms of the T/C ratio [T mean number of days of survival after transplantation in the DC 113 group; C = mean number of days of survival after transplantation in the control group (intraperitoneally given 0.2 ml of PBS)].

TABLE 2

| Test substance | Dose (mg/kg) | Life-prolonging effect (T/C) |
| --- | --- | --- |
| DC113 | 0.013 | 110 |
|  | 0.0063 | 130 |
| Mitomycin C | 6 | 151 |

A method of producing DC 113 is described below.

The novel substance DC 113 can be prepared by cultivating, in an appropriate medium, a microorganism belonging to the genus Streptomyces and capable of producing DC 113 to thereby cause production and accumulation of DC 113 in the culture and recovering DC 113 from the culture.

Any microbial strain belonging to the genus Streptomyces and capable of producing DC 113 can be used as the DC 113-producing strain. Any of mutants derived from such microbial strain by artificial means, such as ultraviolet irradiation, X-ray irradiation or treatment with a mutagen, or by spontaneous mutation may be used in the practice of the invention as long as it can produce DC 113. The strain DO-113 is a typical example.

Bacteriological characteristics of the strain DO-113 are described below. The characteristics were determined by those methods which have been recommended by the International Streptomyces Project (ISP) for the characterization of Streptomyces species [E. B. Shirling and D. Gottlieb: Int. J. Syst. Bacteriol., 16, 313–340 (1966)]. The stereoisomer of diaminopimelic acid in the whole-cell hydrolyzate was identified by the method of B. Becker et al. [Appl. Microbiol., 12, 421–423 (1964)]. The morphological investigations were made under an optical microscope. For spore surface morphology, in particular, a scanning electron microscope was used. The color names given are according to the Color Harmony Manual (Container Corporation of America, 4th edition, 1958).

The bacteriological characteristics of the strain DO-113 are as follows:

(1) Morphology

Aerial mycelium: Branches
Substrate mycelium: Branches but does not fragment.
Spores: Borne on the aerial mycelium in the form of long, flexuous or loop-like chains of 10 to 30 or more arthrospores.
Spore surface: Smooth
Spore motility: Non-motile
Spore shape and size: Elliptic, 0.5×0.7 μm; Neither sclerotium nor sporangium is observable.

(2) Colors

Aerial mycelium: Gray
Substrate mycelium: Light yellow to yellowish brown
Soluble pigment: Cream
Melanoid pigments None (3) Chemical composition of cell wall Stereoisomer of diaminopimelic acid: LL-form (4) Physiological properties Utilization of carbon sources: Utilizes glucose, xylose, inositol, mannitol, arabinose, rhamnose and raffinose; does not utilize fructose, nor sucrose.
Gelatin liquefaction: Negative
Starch hydrolysis: Positive
Skimmed milk coagulation: Negative
Skimmed milk peptonization: Positive
Cellulose degradation: Positive
Growth temperature range: 16°–37° C. (optimum 28°–32° C.).

As for the growth temperature range, the results obtained after 2 days of incubation are shown; as for the actions on gelatin, skimmed milk and cellulose, the results shown are those obtained after 1-month incubation at 28° C.; as for the remaining properties, the results obtained after 2-week incubation at 28° C. are cited.

(5) Growth on various agar media

The results obtained by growing the strain DO-113 on various agar media at 28° C. for 28 days are shown below in Table 3.

TABLE 3

| Medium | Cultural characteristics |
| --- | --- |
| Sucrose-nitrate agar | G: Moderate |
|  | AM: Moderate, slate tan (2 ig) |
|  | SM: Covert brown (2 li) |
|  | P: None |
| Glucose-asparagine agar | G: Good |
|  | AM: Abundant, dark covert gray (2 ih) |
|  | SM: Dark olive (1½ nl) |
|  | P: None |
| Glycerin-asparagine agar | G: Good |
|  | AM: Moderate, natural (2 dc) |
|  | SM: Olive gray (1½ ig) |
|  | P: None |
| Starch agar | G: Good |
|  | AM: Abundant, slate tan (2 ig) |
|  | SM: Beaver gray (3 ml) |
|  | P: None |
| Tyrosine agar | G: Good |
|  | AM: Moderate, griege (1 fe) |
|  | SM: (2 ml) |
|  | P: None |
| Nutrient agar | G: Good |
|  | AM: Covert tan (2 ge) |
|  | SM: Mustard tan (2 lg) |
|  | P: Very light yellow |
| Yeast-malt agar | G: Moderate |
|  | AM: Moderate, beige gray (3 ih) |
|  | SM: Dark brown (3 nl) |
|  | P: Very light yellow |
| Oatmeal agar | G: Good |
|  | AM: Abundant, covert gray (2 fe) |
|  | SM: Ebony (2 PO) |
|  | P: None |
| Peptone-yeast extract-iron agar | G: Moderate |
|  | AM: None |
|  | SM: Bamboo (2 gc) |
|  | P: None |

Abbreviations used: G for extent of growth; AM for extent of development of aerial mycelium and color thereof; SM for color of substrate mycelium; P for color of soluble pigment.

(6) Identification of strain DO-113

The strain DO-113 is of the cell wall type I according to the classification of actinomycetes by M. P. Lechevalier and H. A. Lechevalier [Int. J. Syst. Bacteriol., 20, 435–443 (1970)] since LL-diaminopimelic acid is detectable. Judging from the cell wall type in combination with the morphological characteristics of this strain, it is reasonable to regard the strain as belonging to the genus Streptomyces.

For species identification within the genus, species close in taxonomical characteristics to the strain were searched for among the approved species names found in the Approved Lists of Bacterial Names [V. B. D. Skerman et al.: Int. J. Syst. Bacteriol., 30, 225–420 (1980)] on the basis of the descriptions given by the ISP [Int. J. Syst. Bacteriol., 18, 69–189 (1968); ibid., 18, 279–392 (1968); ibid., 19, 391–512 (1969); ibid., 22, 265–394 (1972); and R. E. Buchanan and N. E. Gibbons (coeditors): Bergey's Manual of Determinative Bacteriology, 8th edition].

The following were employed as key characteristics: grayish mycelium, flexuous or loop-like spore chains, smooth spore surface, no melanoid pigment production, soluble pigment production, and carbon source assimilability pattern.

As a result of searching, three species, namely *Streptomyces griseoaurantiacus*, *Streptomyces nodosus* and *Streptomyces pseudogriseolus*, were found to be close to the strain DO-113.

Type strains of these three species were compared in more detail with the strain DO-113 from the characteristics viewpoint. As a result, the species *Streptomyces griseoaurantiacus* was found to be widely different from the strain DO-113 in that the aerial mycelium of the former has a color in the gray series and a color in the red series and that the substrate mycelium has a color in the red to orange series. *Streptomyces nodosus* was also found to be different from the strain DO-113 in that the substrate mycelium of the former has a greenish yellow color and that the soluble pigment changes in color from red to green depending on the pH. *Streptomyces pseudogriseolus* was found to be substantially different from the strain DO-113 in assimilability of some carbohydrates, namely fructose and raffinose, although they differ little from each other in other respects and resemble each other also in that no soluble pigment is produced in most instances and, if produced, the soluble pigment has a very light yellow color.

Accordingly, the strain DO-113 was identified as a strain of a novel species and named Streptomyces sp. DO-113. This strain has been deposited, since Dec. 26, 1988 (date of original deposit), with the Fermentation Research Institute, Agency of Industrial Science and Technology, Japan under the deposit number FERM BP-2222 in accordance with the Budapest treaty.

Conventional cultivation methods for actinomycetes in general can generally be used in cultivating the strain DO-113. Any of synthetic or natural media may be used as the medium as long as it contains assimilable carbon and nitrogen sources inorganics and other necessary growth-and production-promoting substances, respectively, in appropriate amounts.

Usable as the carbon source are, for example, glucose, starch, dextrin, mannose, fructose, sucrose, lactose, xylose, arabinose, mannitol, and molasses. These may be used either alone or in combination. Furthermore, hydrocarbons, alcohols, organic acids and the like may also be used if the strain employed can assimilate them. Usable as the nitrogen sources are ammonium chloride, ammonium sulfate, ammonium nitrate, sodium nitrate, urea, peptone, meat extract, yeast extract, dry yeast, corn steep liquor, soybean flour, and Casamino acids These may be used either alone or in combination In addition, inorganic salts, such as sodium chloride, potassium chloride, magnesium sulfate, calcium carbonate, potassium dihydrogen phosphate, dipotassium hydrogen phosphate, ferrous sulfate, calcium chloride, manganese sulfate, zinc sulfate and copper sulfate, are added to the medium a necessary. Furthermore, trace components (such as nickel sulfate) capable of promoting the growth of the organism used and/or the production of DC 113 may be added to the medium in appropriate amounts.

Liquid culture, in particular submerged culture with stirring, is best suited for the cultivation of DC 113 producers. A suitable cultivation temperature is within the range of 16°–37° C., particularly within the range of 25°–32° C. The pH of the medium should desirably be maintained at 4 to 10, preferably 6 to 8, by addition of aqueous ammonia or ammonium carbonate solution, for instance.

Generally, after 1 to 7 days of cultivation in liquid culture, the desired substance DC 113 will be produced and accumulated in the culture medium and in bacterial cells.

When the production of DC 113 in the culture has reached a maximum, the cultivation is discontinued.

DC 113 can be isolated and purified from the culture by those conventional means that are generally used for the isolation and purification of microbial metabolites from respective microbial cultures. Thus, for example, the culture is separated into a culture filtrate and cells by filtration, and the cells are subjected to extraction with chloroform, acetone or some other appropriate solvent. The culture filtrate and extract are combined and passed through a column of a polystyrene-based adsorbent, for example Diaion HP20 (Mitsubishi Kasei Corporation), whereby the active component is adsorbed on the adsorbent. The active component is then eluted with ethyl acetate, acetone or the like. The eluate is concentrated and subjected to silica gel column chromatography or high-performance liquid chromatography, for instance, to give DC 113 as light-yellow powder.

The behavior or movement of DC 113 during the cultivation and purification procedures can be followed by means of bioassay using *Bacillus subtilis* No. 10707 or thin layer chromatography followed by ultraviolet irradiation for DC 113 spot detection.

DC 113 can be used as an antibiotic and an antitumor agent in suitable dosage forms prepared by combination with at least one pharmaceutical diluent, adjuvant or carrier For example, DC 113 is usually dissolved in physiological saline, glucose solution, lactose solution or mannitol solution to prepare injections and administered intravenously to mammals, particularly human beings, in a dose of 0.0005–0.5 mg/kg. It may also be administered intraarterially, intraperitoneally or intrathoracically in similar doses. Freeze-drying according to the method specified in Pharmacopoeia of Japan may be applied to solutions containing DC 113, and injectable powder can be prepared by adding sodium chloride. The pharmaceutical preparations of this compound may also contain pharmaceutically acceptable well-known diluents, adjuvants and/or carriers such as pharmaceutically acceptable salts. When DC 113 is used as an injection, it is preferable, in some cases, to use an additive that enhances the solubility of this active ingredient, for example, HCO60 and PEG. It may also be contain a carrier such as liposome and lipid emulsion. Doses of DC 113 may be adjusted appropriately depending on the age and conditions of patients. Administration schedule may also be adjusted depending on the dose, as well as the age and conditions of patients; for example, DC 113 may be intermittently administered every several hours, once a week or once every three weeks, or successively administered once a day. DC 113 may also be orally or rectally administered in similar doses and in the similar manner For oral or rectal administration, it is used in the form of tablets, powder, granules, syrup or suppository with conventional adjuvants.

The antibiotics and antitumor agents thus prepared are expected to to have inhibitory effect on certain tumors. The suitable content of DC 113 in the above antibiotics or antitumor agents is 0.0005 to 0.5 mg in 5 to 20 ml in the case of injection and 0.001 to 85 weight % when they are used in the form of tablets, capsules, powder, granules and suppositories.

The following example illustrates the invention in further detail, but should not be construed to limit the scope of the present invention.

EXAMPLE

Streptomyces sp. DO-113 was used as the seed strain. This strain was inoculated into 300 ml of a seed culture medium (pH 7.2 before sterilization) placed in a 2-liter Erlenmeyer flask. The culture medium was composed of: 5 g/liter Bacto-tryptone (Difco), 5 g/liter yeast extract, 3 g/liter meat extract, 10 g/liter soluble starch, 10 g/liter glucose and 5 g/liter calcium carbonate. Shake culture (200 rpm) was then performed at 30° C. for 48 hours.

The thus-obtained seed culture was transferred to a 30-liter fermentor containing 15 liters of the same medium as mentioned above to an inoculum size of 5% by volume (as the culture) and cultivation was carried out at 28° C. for 24 hours with stirring (200 rpm) and aeration (15 liters of air per minute). The thus-obtained culture was transferred to a 200-liter fermentor containing 100 liters of the same medium as mentioned above to an inoculum size of 10% by volume (as the culture) and cultivation was conducted at 28° C for 24 hours with stirring (180 rpm) and aeration (15 liters of air per minute). The thus-obtained culture was transferred to a 2-kiloliter fermentor containing 1,000 liters of a fermentation medium having the composition specified below to an inoculum size of 10% by volume (as the culture) and cultivation was performed at 28° C. with stirring (120 rpm) and aeration (15 liters of air per minute).

Fermentation medium composition: 50 g/liter soluble starch, 14 g/liter dry yeast, 0.5 g/liter $KH_2PO_4$, 0.5 g/liter $MgSO_4.7H_2O$, 5 g/liter calcium carbonate, 1.0 mg/liter $CuSO_4$, 0.5 mg/liter $NiSO_4.6H_2O$, 1.0 mg/liter $CrK(SO_4)_2.12H_2O$, pH adjusted to 7.0 with NaOH before sterilization.

During cultivation, the pH of the medium was not adjusted at all. After 90 hours of cultivation, 500 liters of n-propanol was added to the culture, the mixture was stirred and the cells and precipitate were filtered off. The filtrate thus obtained amounted to 1,500 liters.

The filtrate was passed through a column packed with 50 liters of Diaion HP20 (polystyrene-based adsorbent) for adsorption of the active substance. After impurity elution with deionized water and 30% methanol, the active substance was eluted with ethyl acetate. Active fractions were combined and concentrated, water was added, and the resulting mixture was extracted again with ethyl acetate. Concentration of the ethyl acetate layer gave 200 g of a yellow oil. The oil was applied to a silica gel (Art 7734; Merck) column and, after impurity elution with hexane and with hexane-ethyl acetate (2:8 v/v), the active substance was eluted with ethyl acetate and with ethyl acetate-methanol (95:5 v/v). Active substance-containing fractions were combined and concentrated, the residue obtained was applied to a column packed with aminopropyl silica gel (Y-8025, available from Yamazen), followed by elution with toluene and with toluene-acetone (8:2 v/v). Active fractions were combined and concentrated and the residue was subjected to high-performance liquid chromatography using reversed-phase silica gel (YMC ODS SH-363-5; YMC) as the packing and 70% methanol as the solvent. Thus was recovered 30 mg of DC 113 as a light-yellow powder.

While the invention has been described in detail and with reference to specific embodiments thereof, it will be apparent to one skilled in the art that various changes and modifications can be made therein without departing from the spirit and scope thereof.

What is claimed is:

1. A compound represented by the formula:

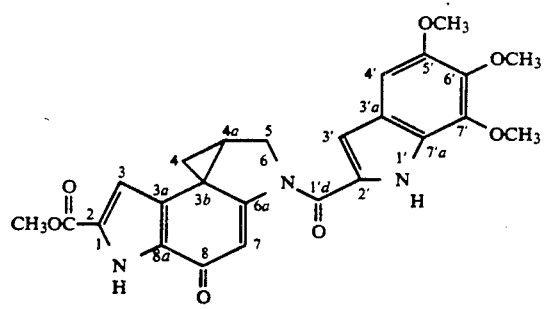

* * * * *

UNITED STATES PATENT AND TRADEMARK OFFICE
CERTIFICATE OF CORRECTION

PATENT NO. : 5,101,038

DATED : March 31, 1992

INVENTOR(S) : HIROFUMI NAKANO ET AL.          Page 1 of 2

It is certified that error appears in the above-identified patent and that said Letters Patent is hereby corrected as shown below:

ON THE TITLE PAGE

At item [56] References Cited
       U.S. Patent Documents, "4,423,229  11/1983  Wierenga"
           should read --4,423,229  12/1983  Wierenga--.

Foreign Patent Documents, "2115184  4/1990  Japan"
           should read --2-115184  4/1990  Japan--.

AT [57] ABSTRACT

Formula, "1'd" should read --1'a--.

COLUMN 2

Line 7, "formula" should read --formula:--.
       Line 13, "{sh," should read --(sh,--.

COLUMN 5

Line 56, "sources" should read --sources,--.
       Line 57, "growth-and" should read --growth- and--.
       Line 68, "acids" should read --acids.--.

COLUMN 6

Line 1, "combination In" should read --combination.  In--.
       Line 7, "a" should read --as--.
       Line 51, "carrier For" should read --carrier.  For--.
       Line 67, "be" should be deleted.

UNITED STATES PATENT AND TRADEMARK OFFICE
CERTIFICATE OF CORRECTION

PATENT NO. : 5,101,038

DATED : March 31, 1992

INVENTOR(S) : HIROFUMI NAKANO ET AL.    Page 2 of 2

It is certified that error appears in the above-identified patent and that said Letters Patent is hereby corrected as shown below:

COLUMN 7

Line 9, "manner For" should read --manner. For--.
    Line 13, "to to" should read --to--.

COLUMN 8

Formula, "1'd" should read --1'a--.

Signed and Sealed this

Twentieth Day of July, 1993

Attest:

MICHAEL K. KIRK

Attesting Officer    Acting Commissioner of Patents and Trademarks